United States Patent [19]

Schirmann et al.

[11] Patent Number: 5,239,119
[45] Date of Patent: Aug. 24, 1993

[54] CATALYTIC SYNTHESIS OF AZINES FROM $H_2O_2/NH_3$/CARBONYL COMPOUNDS

[75] Inventors: Jean-Pierre Schirmann, Oullins; Pierre Tellier, Sainte Foy Les Lyon, both of France

[73] Assignee: Atochem, Puteaux, France

[21] Appl. No.: 797,356

[22] Filed: Nov. 25, 1991

[30] Foreign Application Priority Data

Nov. 23, 1990 [FR] France .................................. 90 14634

[51] Int. Cl.$^5$ ........................................... C07C 249/16
[52] U.S. Cl. ..................................................... 564/249
[58] Field of Search ........................................ 564/249

[56] References Cited

U.S. PATENT DOCUMENTS

| | | | |
|---|---|---|---|
| 3,869,541 | 3/1975 | Weiss et al. | 260/240 G |
| 3,943,152 | 3/1976 | Tellier et al. | 260/345.1 |
| 3,972,876 | 8/1976 | Schirmann et al. | 423/407 |
| 3,972,878 | 8/1976 | Schirmann et al. | 260/240 G |
| 4,093,656 | 6/1978 | Schirmann et al. | |

*Primary Examiner*—Richard L. Raymond
*Assistant Examiner*—P. O'Sullivan
*Attorney, Agent, or Firm*—Burns, Doane, Swecker & Mathis

[57] ABSTRACT

Azines are synthesized from aqueous hydrogen peroxide, ammonia and a carbonyl compound, e.g., acetone, methyl ethyl ketone or methyl isobutyl ketone, in the presence of a catalytically effective amount of immixture of an amide of a weak acid and an ammonium salt corresponding to such weak acid. A more general high output such process comprises (a) interreacting aqueous hydrogen peroxide, ammonia and a carbonyl compound in the presence of a catalytically effective amount of immixture comprising an amide of a weak acid, (b) separating the azine thus produced from the medium of reaction, (c) reconstituting the amount of the amide in the medium of reaction to the initial amount thereof present at the onset of step (a), and (d) recycling such reconstituted medium of reaction to step (a).

17 Claims, No Drawings

CATALYTIC SYNTHESIS OF AZINES FROM H₂O₂/NH₃/CARBONYL COMPOUNDS

BACKGROUND OF THE INVENTION

1. Field of the Invention

The present invention relates to the synthesis of azines and more especially, to the production of hydrazine.

2. Description of the Prior Art

Hydrazine, typically in the form of hydrazine hydrate, is a widely used compound, whether as such or as a synthesis intermediate. According to Ullmann, 5th edition, vol. A 13, pages 177-191 (1989), hydrazine is produced either by the oxidation of ammonia with chlorine or a hypochlorite bleach solution, optionally via a ketazine, or by reacting aqueous hydrogen peroxide with ammonia and a ketone.

The aqueous hydrogen peroxide process is well known to this art and has been described, for example in U.S. Pat. Nos. 3,972,878, 3,972,876, 3,869,541, 3,948,901, 3,919,256, 3,943,152 and 4,093,656.

In this process, ammonia, aqueous hydrogen peroxide and a compound bearing a $>C=O$ group, such as a ketone, are interreacted according to the following reaction scheme:

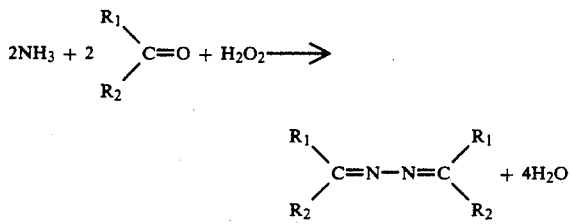

The reaction is carried out in the presence of catalyst.

The azine can then be hydrolyzed into hydrazine hydrate according to the mechanism:

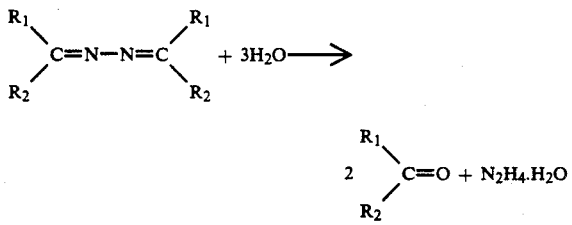

with the ketone being regenerated.

U.S. Pat. No. 3,972,878 describes such reaction in the presence of a mixture of an amide of a weak acid and of a phosphate. Such mixtures include, for example, acetamide with lithium phosphate, acetamide with sodium carbonate, propionamide with lithium phosphate, acetamide with disodium phosphate and acetamide with diisopropyl phosphate.

The azine yield based on the aqueous hydrogen peroxide ranges from 45% to 55% and increases to 78% when using the acetamide/disodium phosphate pair.

U.S. Pat. No. 4,093,656 also describes, in a reaction for the synthesis of azines, a catalyst which is a mixture of three compounds, namely, an amide of a weak acid, the ammonium salt corresponding to this acid and another compound such as a phosphate. Such mixtures include, for example, admixture of acetamide, ammonium acetate and sodium phosphate. The azine yield based on the aqueous hydrogen peroxide is as high as 85%.

SUMMARY OF THE INVENTION

A major object of the present invention is the provision of improved process for the aqueous H₂O₂ synthesis of azines in very high yields, such process being carried out in the presence of a catalyst consisting essentially of an immixture of an amide of a weak acid and of the corresponding ammonium salt of such weak acid.

Briefly, the present invention features a process for the synthesis of azines from aqueous hydrogen peroxide, ammonia and from a carbonyl compound reactant, comprising contacting such reactants with a catalytically effective amount of an amide of a weak acid and the ammonium salt corresponding to such acid, and thereafter isolating the azine thus produced.

This invention also features a high output, more generic process for the synthesis of azines, comprising (a) interreacting aqueous hydrogen peroxide, ammonia and a carbonyl compound in the presence of a catalytically effective amount of immixture comprising an amide of a weak acid, (b) separating the azine thus produced from the medium of reaction, (c) reconstituting the amount of said amide in the medium of reaction to the initial amount thereof present at the onset of step (a), and (d) recycling such reconstituted medium of reaction to step (a).

DETAILED DESCRIPTION OF THE PREFERRED EMBODIMENTS OF THE INVENTION

More particularly according to the present invention, the aqueous hydrogen peroxide is advantageously employed in its usual commercial form, for example as an aqueous solution containing from 30% to 90% by weight of H₂O₂. One or more conventional stabilizers for peroxide solutions may advantageously be added thereto, for example the sodium salt of ethylenediaminetetracetic acid.

The ammonia may be anhydrous or in aqueous solution.

The carbonyl compound characteristically has the formula:

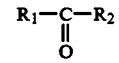

in which R₁ and R₂, which may be identical or different, are each hydrogen, an alkyl radical having from 1 to 12 carbon atoms, a branched alkyl or cycloalkyl radical having from 3 to 12 carbon atoms, or an aromatic radical having from 6 to 12 carbon atoms, with the proviso that R₁ and R₂ may together form a linear or branched alkylene radical having from 3 to 12 carbon atoms, and with the further proviso that such radicals R₁ and R₂ may be substituted by a halogen, NO₂, hydroxyl, alkoxy or carboxylic ester group, preferably by Cl, NO₂ or CH₃O.

Exemplary such reactants:

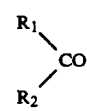

include the aldehydes and ketones.

Representative of the aldehydes are formaldehyde, acetaldehyde, butyraldehyde, isobutyraldehyde, n-pentanal, pivalaldehyde, benzaldehyde, monochlorobenzaldehydes, paranitrobenzaldehyde, anisaldehyde, beta-chloropropionaldehyde and beta-methoxypropionaldehyde.

Representative ketones are acetone, 2-pentanone, 3-pentanone, methyl isopropyl ketone, methyl isobutyl ketone, methyl ethyl ketone, methyl cyclohexyl ketone, acetophenone, benzophenone, cyclobutanone, cyclopentanone and cyclohexanone.

Ketones in which $R_1$ and $R_2$ are identical or different and are linear or branched alkyl radicals having from 1 to 5 carbon atoms are advantageously employed, and preferably acetone; methyl ethyl ketone and methyl isobutyl ketone.

The above reactants can be employed in stoichiometric amounts, but 0.2 to 5 moles and preferably 1.5 to 4 moles of the carbonyl compound reactant (aldehyde or ketone) and 0.1 to 10 moles and preferably 1.5 to 4 moles of ammonia are advantageously employed per mole of aqueous hydrogen peroxide.

The amides according to the present invention are derived from the corresponding carboxylic acids which have a dissociation constant less than $5 \times 10^{-5}$, namely, acids which have a pK greater than 4.3 in aqueous solution at 25° C.

In the case of polycarboxylic acids, these are acids whose first ionization constant is less than $5 \times 10^{-5}$.

Exemplary thereof are carboxylic acids of the formula $R_5COOH$ in which $R_5$ is a linear alkyl radical having from 1 to 20 carbon atoms or a branched or cyclic alkyl radical having from 3 to 12 carbon atoms, or an optionally substituted phenyl radical, polycarboxylic acids of the formula $R_6(COOH)_n$ in which $R_6$ is an alkylene radical having from 1 to 10 carbon atoms and n is 1 or 2, with the proviso that $R_6$ may be a single valence bond and in this instance n has the value of 2. The radicals $R_5$ and $R_6$ may be substituted by halogens or OH, $NO_2$ or methoxy groups.

Acetamide, propionamide, n-butyramide or isobutyramide are the preferred amides.

The ammonium salt corresponding to acetamide, for example, is ammonium acetate.

It is also within the scope of the invention to from the ammonium salt in situ, namely, by employing the corresponding carboxylic acid which produces the ammonium salt by reaction with ammonia.

The proportions of the amide and of the corresponding ammonium salt may vary over wide limits. Advantageously, from 1 to 25 parts of the ammonium salt, and preferably 2 to 10, are typically employed per 5 parts of amide.

The amount of the amide may also vary over wide limits.

The contact between the aqueous hydrogen peroxide, ammonia and the reactant bearing a carbonyl functional group with the amide and the ammonium salt may be carried out in any manner.

The operation is advantageously carried out in a homogeneous medium or in a medium which ensures at least a sufficient solubilization of the reactants to permit obtaining the azine. The reaction can be carried out over a very wide temperature range, for example from 0° to 100° C., and advantageously from 30° to 70° C.

Although it is possible to carry out the operation at any pressure, it is simpler to operate at atmospheric pressure. It is also possible to operate at pressures up to approximately 10 bar if necessary, preferably to maintain the reaction in liquid phase.

The reactants may be introduced simultaneously, or separately, and in any order whatsoever. Reactors of any type, stirred or unstirred, may be employed, or even simple reaction vessels which may be arranged in parallel, in series with cocurrent flow or countercurrent flow, or any other combination of such options.

The amide and the ammonium salt are typically employed in the form of an aqueous solution thereof.

This solution may also include an alcohol. Exemplary such alcohols advantageously employed include saturated aliphatic alcohols having from 1 to 6 carbon atoms and preferably 1 to 2 carbon atoms.

Diols are also advantageously employed, and more particularly diols having from 2 to 5 carbon atoms. Exemplary thereof are ethylene glycol, propylene glycol, 1,3-propanediol, 1,3- and 1,4-butanediol and 1,5-pentanediol.

Upon completion of the reaction, the azine may be recovered by distillation, liquid/liquid extraction or any equivalent means, or even wholly or partially simply by phase separation if it is insoluble in the reaction mixture.

After the azine has been recovered from the reaction mixture, there remains a solution containing amide and ammonium salt and possibly ammonia, the carbonyl compound reactant, aqueous hydrogen peroxide and various byproducts or impurities.

As much of the ammonia and of the carbonyl compound reactant as possible is then recovered in order to recycle them, advantageously, back into the synthesis reaction.

One advantage of the process of the invention is that it avoids the use of compounds such as phosphates, which complicate the subsequent treatment of the solution of amide and ammonium salt. Aqueous hydrogen peroxide is difficult to recycle and the operation is carried out under such conditions that it is completely consumed.

Whether the synthesis of azines is carried out entirely (i) in the presence of an amide of a weak acid and of the corresponding ammonium salt as described above, or (ii) in the presence of an amide of a weak acid, of the corresponding ammonium salt and of a compound such as a phosphate as described in U.S. Pat. No. 4,9093,656, or (iii) in the presence of an amide of a weak acid and of a compound such as a phosphate as described in U.S. Pat. No. 3,972,878, the present invention also features the treatment of the solutions containing these compounds in order to recycle them into a synthesis of azines beginning with aqueous hydrogen peroxide, ammonia and a carbonyl compound reactant.

The present invention thus features a process for the synthesis of azines from aqueous hydrogen peroxide, ammonia and a carbonyl compound reactant, comprising:

(a) contacting such reactants with a mixture containing an amide of a weak acid, (b) separating from such reaction medium the azine thus produced, (c) reconstituting said reaction medium to the beginning amount of the starting material amide in step (a), and (d) recycling the mixture obtained from step (c) to step (a).

The carbonyl compound reactant is the same as that described above. The mixture containing the amide is one of the three mixtures described above, i.e., it also contains a compound which may be a phosphate as described in U.S. Pat. No. 3,972,878 or additionally containing the corresponding ammonium salt as described in U.S. Pat. No. 4,093,656, or else it is the mixture of an amide of a weak acid and of the corresponding ammonium salt according to the present invention.

Indeed, it has now been found that, upon completion of step (a), a fraction of the amide is converted into the corresponding ammonium salt, namely, if acetamide is employed in step (a), then acetamide and ammonium acetate are obtained.

As indicated above, after the step (a) of synthesis, the azine is recovered in step (b) and a solution remains, containing a portion of the amide introduced and the ammonium salt corresponding to this amide. The number of moles of the remaining amide added to the number of moles of the corresponding ammonium salt is substantially equal to the number of moles of amide introduced in step (a). This solution additionally contains the compound which accompanied the amide at the beginning of step (a); this product may be the corresponding ammonium salt or phosphate or a mixture of both (salt and phosphate), i.e., if acetamide and phosphate were present in step (a) at the beginning of reaction, then a solution of acetamide, ammonium acetate and phosphate is obtained. If acetamide and acetate were present in step (a) at the beginning, then a solution with less acetamide and more acetate is obtained. If acetamide, acetate and phosphate were present in step (a) at the beginning, then a solution with less acetamide, more acetate and phosphate is obtained. After the azine has been removed, this solution may also contain impurities and excess reactants: ammonia and the carbonyl compound reactant. It is advantageous to recover these excess reactants: ammonia and the carbonyl compound reactant. It is advantageous to recover these excess reactants. Step (c) is then carried out, i.e., the ammonium salt is converted into the corresponding amide until the initial amide of step (a) is regenerated. One advantageous means for effecting this result entails, for example, simple heating. This reaction is per se known to the art. When this step (c) is carried out by heating, a reversion of the ammonium salt into the amide is therefore obtained to reconstitute the mixture containing an amide of step (a). This reaction may also be accompanied by a decomposition of a proportion of the ammonium salt into ammonia and the corresponding acid.

The ammonia and the acid are remixed to reform the ammonium salt, which is recycled.

If the mixture to be reconstituted for carrying out step (a) is a mixture containing an amide and the corresponding ammonium salt, then there is no disadvantage in the fact that the regeneration in step (c) produces a mixture of amide and corresponding acid. It suffices, indeed, to add ammonia to this mixture before recycling it to step (a) or, preferably, to provide an excess of ammonia in step (a) to reform this ammonia salt in situ. Compare, for example, *J. American Chemical Society*, pages 1879 to 1883 (May 1931). Heating to at least 160° C. and preferably from 170° to 230° C., is carried out. The heating is preferably accomplished by distilling water. If the mixture to be reconstituted for carrying out step (a) is a mixture containing an amide and the corresponding ammonium salt, the operation of step (c) therefore entails converting the amide/ammonium salt mixture which is depleted in amide and enriched in ammonium salt during step (a), by converting some of the salt to amide. It is also within the scope of the invention to conduct step (c) on only a portion of the solution, namely, if, after step (b), only a portion of the solution which is rich in ammonium salt and low in amide were treated in step (c) and then remixed with the untreated portion. As indicated above, some of the ammonium salt may be in the form of acid; ammonia is then added to obtain the ammonium salt again.

Step (d) is then carried out. It is found that azine can be produced when this solution is recycled to step (d). If this treatment of step (c) is not conducted before carrying out step (d), then a lower output of azines is attained than during the preceding synthesis and after 2 or 3 recycles the output is very low.

In a preferred embodiment of the invention, some high-boiling impurities may be removed from the solution obtained at the end of step (c). The removal of these high-boiling impurities can be effected quite simply, by distillation. This amount of impurities represents from 0.01% to 5% by weight of the total solution.

This amount is low and may depend on the conditions of the azine synthesis, the impurities already present in the ammonia, the aqueous hydrogen peroxide and the carbonyl compound reactant, and it is known that under these conditions aqueous hydrogen peroxide can produce heavy impurities.

Instead of being carried out by distillation, these impurities can also be removed by passing the solution over absorbent microporous particles. For example, the materials described in U.S. Pat. No. 4,657,751 may be used before the solution containing the amide and possibly the corresponding ammonium salt is recycled. If need be, phosphate or any additive which accompanied the acid and the ammonium salt during step (a) is replenished.

It will be appreciated that the step (c) comprises regenerating the fraction of the amide which has been converted into the corresponding ammonium salt. If the amide and the corresponding ammonium salt were used in step (a), only a proportion of the ammonium salt is regenerated such as to reconstitute the initial mixture of amide and ammonium salt.

In order to further illustrate the present invention and the advantage thereof, the following specific examples are given, it being understood that same are intended only as illustrative and in nowise limitative.

EXAMPLE 1

The following reactants were introduced into a 250-ml reactor fitted with a stirrer, a condenser and a dip tub connected to an ammonia reserve:
 (i) water: 29 grams,
 (ii) acetamide: 59 grams (1 mole),
 (iii) ammonium acetate: 64 grams (0.83 moles),
 (iv) sodium salt of ethylenediaminetetraacetic acid: 0.1 gram (stabilizer for $H_2O_2$),
 (v) methyl ethyl ketone: 72 grams (1 mole).

Ammonia gas was introduced through the dip tube to saturation and the temperature was increased to 50° C.

24.3 grams of an aqueous solution containing 70% by weight of hydrogen peroxide (0.5 moles) were then introduced over 30 minutes while the ammonia stream was maintained.

After 8 hours, 30 min, of reaction, the reactor was cooled and the two phases (organic and aqueous) were separated by gravity separation. A determination of the hydrogen peroxide (by iodometry and of the azine (by vapor phase chromatograph) was carried out on each phase.

The aqueous phase contained 0.016 moles of hydrogen peroxide and 0.018 moles of methyl ethyl ketone azine.

The organic phase contained 0.005 moles of peroxide
Hydrogen peroxide conversion: 95.8%
Selectivity: 86%
Yield: 82.4%

EXAMPLE 2

The procedure of Example 1 was repeated, except that, in addition, 0.5 gram of disodium phosphate was introduced at the outset.

After 8 hours, 30 min, of reaction, the aqueous phase contained 0.023 moles of hydrogen peroxide and 0.014 moles of azine. The organic phase contained 0.003 moles of hydrogen peroxide and 0.391 moles of azine.
Hydrogen peroxide conversion: 96.8%
Selectivity: 83.7%
Yield: 81%

EXAMPLE 3

An azine synthesis was carried out using methyl ethyl ketone and a mixture of acetamide and disodium phosphate; upon completion of step (a), the MEK azine was insoluble. It was separated off by gravity separation and an aqueous phase remained.

The aqueous phase exiting the reactors was subjected to a wash with the methyl ethyl ketone recycled from the hydrolysis in order to extract the azine contained therein. A fresh aqueous was obtained. It corresponded to the following average composition (weight %):

$H_2O_2 = 0.2\%$
$NH_3 = 5.2\%$
MEK* = 3.5%
Acetamide = 19.7%
Ammonium acetate = 32.5%
$H_2O = 38.8\%$
Azine = 0.1%
Impurities = remainder * MEK = Methyl ethyl ketone
One half of this aqueous phase was reconstituted (step (c)).

Apparatus Employed

The laboratory apparatus employed was:
(i) a laboratory adiabatic Oldershaw column with perforated trays of internal diameter 0=20 mm, and comprising 20 trays,
(ii) a titanium boiler of 250 cm³ volume,
(iii) a condenser,
(iv) a reflux vessel,
(v) plunger metering pumps which made it possible to ensure the introduction of the mixture, the draining of the boiler and the introduction of the reflux,
(vi) the reflux was determined by virtue of a flow meter with a precalibrated float,
(vii) boiler heating was provided by a metal bath maintained at 200° C. by virtue of a temperature control,
(viii) the drainage pipework and the head of the draining pump were maintained at 80° by virtue of a jacket in which hot oil was circulated, such as to avoid any setting solid.

Operating Conditions

The introduction of the mixture to be treated was into the boiler at a rate of 249.5 g/hour.

In normal operation, the temperatures were as follows:
Boiler: 180°–1181°
Tray 10:135°
Head:94°–95°
The reflux ratio was 0.1.
The residence time in the boiler was 1 hour, 30 min.
190.5 g/hour of distillate were collected overhead, having the following composition:
$NH_3$: 14.7%
MEK: 6.6%
$H_2O$:78.5%
Azine: 0.1%
Acetate: 0

159 g/hour of a solution of the following composition were obtained by draining the boiler:
Acetic acid: 21.5%
Acetate: 2.6%
Acetamine: 73.6%
$H_2O$: 2.2%
MEK: traces
Azine: Traces These boiler drainings were remixed with the untreated other half and then recycled to step (a).

The ammonia collected overhead was partially separated from the water and was then also recycled to step (a).

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of an azine, comprising interreacting aqueous hydrogen peroxide, ammonia and a carbonyl compound in the presence of a catalytically effective amount of immixture consisting essentially of an amide of a weak acid and the ammonium salt corresponding to such acid, and thereafter separating the azine thus produced from the medium of reaction.

2. The process as defined by claim 1, said carbonyl compound having the formula:

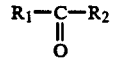

in which $R_1$ and $R_2$, which may be identical or different, are each hydrogen, an alkyl radical having from 1 to 12 carbon atoms, a branched alkyl or cycloalkyl radical having from 3 to 12 carbon atoms, or an aromatic radical having from 6 to 12 carbon atoms, with the proviso that $R_1$ and $R_2$ may together form a linear or branched alkylene radical having from 3 to 12 carbon atoms, and with the further proviso that such radicals $R_1$ and $R_2$ may be substituted by at least one halogen, $NO_2$, hydroxyl, alkoxy or carboxylic ester group.

3. The process as defined by claim 2, said carbonyl compound comprising formaldehyde, acetaldehyde, butyraldehyde, isobutyraldehyde, n-pentanal, pivalaldehyde, benzaldehyde, monochlorobenzaldehydes, paranitrobenzaldehyde, anisaldehyde, beta-chloropropionaldehyde or beta-methoxyproprionaldehyde.

4. The process as defined by claim 2, said carbonyl compound comprising acetone, 2-pentanone, 3-pentanone, methyl isopropyl ketone, methyl isobutyl ketone, methyl ethyl ketone, methyl cyclohexyl ketone, acetophenone, benzophenone, cyclobutanone, cyclopentanone or cyclohexanone.

5. The process as defined by claim 2, said carbonyl compound comprising acetone, methyl ethyl ketone or methyl isobutyl ketone.

6. The process as defined by claim 1, comprising interreacting 0.2 to 5 moles of said carbonyl compound and 0.1 to 10 moles of ammonia per mole of aqueous hydrogen peroxide.

7. The process as defined by claim 1, said amide of a weak acid having a dissociation constant of less than $5 \times 10^{-5}$.

8. The process as defined by claim 7, said amide of a weak acid comprising acetamide, propionamide, n-butyramide or isobutyramide.

9. The process as defined by claim 1, said immixture comprising 1 to 25 parts by weight of said ammonium salt per 5 parts by weight of said amide.

10. The process as defined by claim 1, wherein the medium of reaction further comprises an alcohol.

11. A process for the preparation of an azine, comprising (a) interreacting aqueous hydrogen peroxide, ammonia and a carbonyl compound in the presence of a catalytically effective amount of immixture comprising an amide of a weak acid, (b) separating the azine thus produced from the medium of reaction, (c) reconstituting the amount of said amide in the medium of reaction to the initial amount thereof present at the onset of step (a) by regenerating said amide from ammonium salt generated during the reaction of step (a), and (d) recycling such reconstituted medium of reaction to step (a).

12. The process as defined by claim 11, said immixture comprising an ammonium salt corresponding to said weak acid.

13. The process as defined by claim 11, said immixture comprising a co-catalyst compound.

14. The process of claim 11, wherein said amide is regenerated by heating the medium of reaction to a temperature sufficient to achieve reversion of said ammonium salt back to said amide.

15. The process of claim 11, wherein an excess of ammonia is added to the reconstituted medium of reaction prior to recycling.

16. The process of claim 11, wherein said reconstituting of said amide is completed on a portion of said reaction medium, said portion being less than the entire reaction medium.

17. The process of claim 11, further comprising removing high-boiling impurities at the end of step (c) by distillation or passing the solution over absorbent microporous particles.

* * * * *